United States Patent [19]

Strosberg et al.

[11] Patent Number: 4,859,595

[45] Date of Patent: Aug. 22, 1989

[54] METHOD FOR PREPARING RABBIT MONOCLONAL ANTIBODIES, THE CELL LINES USED THEREIN AND THE ANTIBODIES PRODUCED THEREBY

[76] Inventors: Arthur D. Strosberg, 66 rue de Javel, 75105 Paris, France; Jean-Gerard Guillet, 2 rue de Wattignies, 75012 Paris, France

[21] Appl. No.: 730,346

[22] Filed: May 3, 1985

[51] Int. Cl.⁴ .................. C12N 15/00; C12N 5/00; C12R 1/91
[52] U.S. Cl. ..................... 435/172.2; 435/240.27; 435/948; 935/110; 935/102
[58] Field of Search ............ 435/68, 172.2, 240, 435/241, 948; 935/102, 110; 424/85, 86; 436/548

[56] References Cited

U.S. PATENT DOCUMENTS 4,491,632 1/1985 Wands et al. ............... 424/86

OTHER PUBLICATIONS

Dreher et al., Journal of Immunology 130(1), pp. 442–448 (1983).
Braun et al., Hoppe–Seyler's Z. Physiol. Chem., 360(5) pp. 663–678, (1979), Biological Abst. 68:53873.
Hoebeke et al., Dev. Immunol. 18, p. 307–11 (1983), Chemical Abst. 100:17099v.
Kohler and Milstein, Nature, 256 495–497 (1975).
J. J. Collins et al., P.N.A.S., 71, 260–263 (1974).
A. D. Strosberg et al., P.N.A.S., 71, 263–265 (1974).
Petit-Koskas et al., Eur. J. Immunology, 11, 388–92 (1981).

Primary Examiner—John E. Tarcza
Attorney, Agent, or Firm—Willian Brinks Olds Hofer Gilson & Lione

[57] ABSTRACT

A new continuous rabbit cell line, designated TP-3, and variants thereof, which are hypoxyxanthineguanine-phosphoribosyl transferase deficient, hypoxyxanthine-aminopterine-thymidine sensitive, fast growing and non-antibody producing, and the methods for preparing the TP-3 cell line. Also, rabbit-rabbit hybrid cells formed by fusing the TP-3 cell line with antibody-producing cells from immunized rabbits, which hybrid cells are hypoxyxanthine-aminopterine-thymidine insensitve and secrete rabbit antibodies, and the methods for preparing the hybrid cells and hybrid cell lines. The invention further comprises rabbit monoclonal antibody.

11 Claims, 6 Drawing Sheets

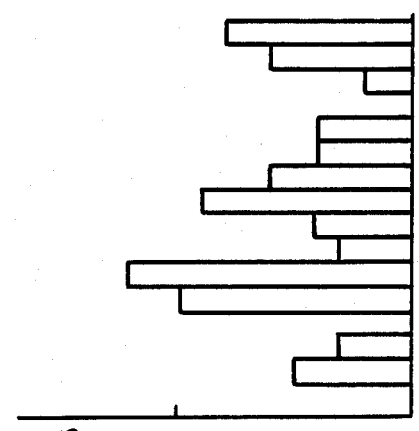
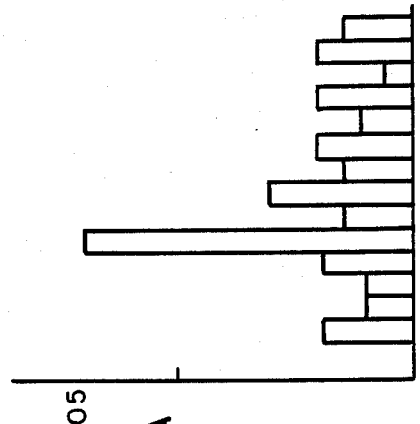

METHOD FOR PREPARING RABBIT MONOCLONAL ANTIBODIES, THE CELL LINES USED THEREIN AND THE ANTIBODIES PRODUCED THEREBY

BACKGROUND OF THE INVENTION

The present invention relates to monoclonal rabbit antibody and to methods for producing monoclonal rabbit antibody. The invention further relates to a new rabbit-rabbit hybrid cell capable of producing monoclonal rabbit antibody and to the methods for producing the hybrid cells. Finally, the invention relates to a new rabbit cell line capable of being fused with an antibody-producing cell from an immunized rabbit to form a hybrid cell which produces monoclonal antibody and to the methods for producing this new rabbit cell line.

Antibodies are complex molecules which are produced by the immune systems of animals to protect the animal against foreign substances. Antibodies are generally obtained by immunizing an animal by injecting it with a foreign substance which will stimulate the animal's immune system. The antibodies produced to a particular foreign substance are actually a heterogeneous mixture of several different antibodies (polyclonal antibodies) which recognize various antigenic determinants on the foreign substance. A number of problems are associated with the use of polyclonal antibody. Polyclonal antibody has a limited availability. Further, it is practically impossible to completely separate antibodies having different antigenic reactivities from each other, and even the most carefully purified antibody fractions may react with more than one substance.

In the seminal work of Kohler and Milstein, *Nature*, 256, 495-97 (1975), a procedure for the fusion of mouse myeloma cells to spleen cells from immunized mice to obtain a cell line producing homogeneous monoclonal antibody was first described. The production of monoclonal antibodies from hybridoma cell lines derived by cell fusion techniques from an appropriate cell line has also been described for rat and human. In each of these species, myeloma cell lines existed which could be fused with lymphoid cells from immunized mice, rats or humans. The resulting hybridoma cells produced monoclonal antibodies against the immunogen with which the mice, rats or humans had been immunized.

The use of monoclonal antibodies circumvents several of the major problems associated with the use of polyclonal antibodies found in the antisera of immunized animals. Since hybridomas may be cloned and because hybridoma cell lines are immortal, monoclonality, monospecificity and permanent availability of the monoclonal antibody are assured.

Immune responses against a large variety of antigens have been studied primarily in rabbits, and rabbits are known to produce antibodies of high affinity and wide specificity. Consequently, rabbit antibodies are often used in basic research studies and in industrial and medical procedures.

As in other species, the heterogeneity of the antibodies present in rabbit antisera produced by live animals and the limited availability of well-characterized antibodies have become major obstacles for further use of rabbit antibodies in standardized diagnostic tests and in therapeutic procedures. Unfortunately, in contrast to the aforementioned species, no potential rabbit myeloma parent cell lines are available for use in the preparation of hybrid cells.

In 1974, J. J. Collins et al., *P.N.A.S.*, 71, 260-63 (1974) and A. D. Strosberg et al., *P.N.A.S.*, 71, 263-65 (1974), reported the preparation of a stable antibody-producing but antibody-non-secreting rabbit cell line, designated TRSC-1, obtained by in vitro transformation of splenocytes by Simian Virus 40 (SV40). In 1981, Petit-Koskas et al., *Eur. J. Immunol.*, 11, 388-92 (1981) described the use of 0.02% ethylmethyl sulfonate (EMSF) to cause the mutation of the TRSC-1 cell line. Exposure to EMSF was followed by selection in an 6-thioguanine-containing medium to obtain a stable hypo-xanthine-guanine-phosphoribosyl transferase deficient (HGPRT−) mutant cell line, designated TRSC-1-8, which is sensitive to aminopterine. The TRSC-1-8 cell line was used in cell fusion experiments with lymph node lymphocytes from rabbits immunized with various antigens. Although hybrid cells were obtained, none produced complete immunoglobulin molecules or active antibodies.

Accordingly, it is an object of this invention to produce a stable rabbit parent cell line capable of fusing with antibody-producing cells from immunized rabbits to form hybrid cells capable of producing monoclonal rabbit antibodies. It is a further object of the invention to produce a hybrid cell line and to produce monoclonal rabbit antibodies. Finally, it is an object of this invention to develop the methods for producing said stable parent cell line and said hybrid cell line.

BRIEF DESCRIPTION OF THE INVENTION

A method to produce a stable parent rabbit cell line has been developed. The new cell line, designated TP-3, was derived from rabbit splenocytes. The splenocytes were first transformed by SV40 and were then treated with ESF to produce an HGPRT−, extremely hypoxanthine, aminopterine and thymidine (HAT) sensitive, fast growing, non-antibody-secreting, continuous cell line. The TP-3 cells fuse with antibody-producing cells from immunized rabbits to produce a novel rabbit-rabbit hybrid cell which is HAT insensitive and which produces rabbit monoclonal antibody to a wide range of haptens and antigens.

The monoclonal antibodies may be used in any way that polyclonal antibodies are now used. Consequently, they should find use in immunoassays and passive immunization, in research and in the diagnosis and treatment of numerous diseases.

BRIEF DESCRIPTION OF THE DRAWINGS

FIG. 3: Results of an ELISA test for anti-NT antibodies in the supernatants of several positive hybrid cell subclones on Day 3 of culture (A), Day 5 of culture (B), Day 6 of culture (C), and Day 7 of culture (D).

DETAILED DESCRIPTION OF THE PREFERRED EMBODIMENTS

Figure 1:
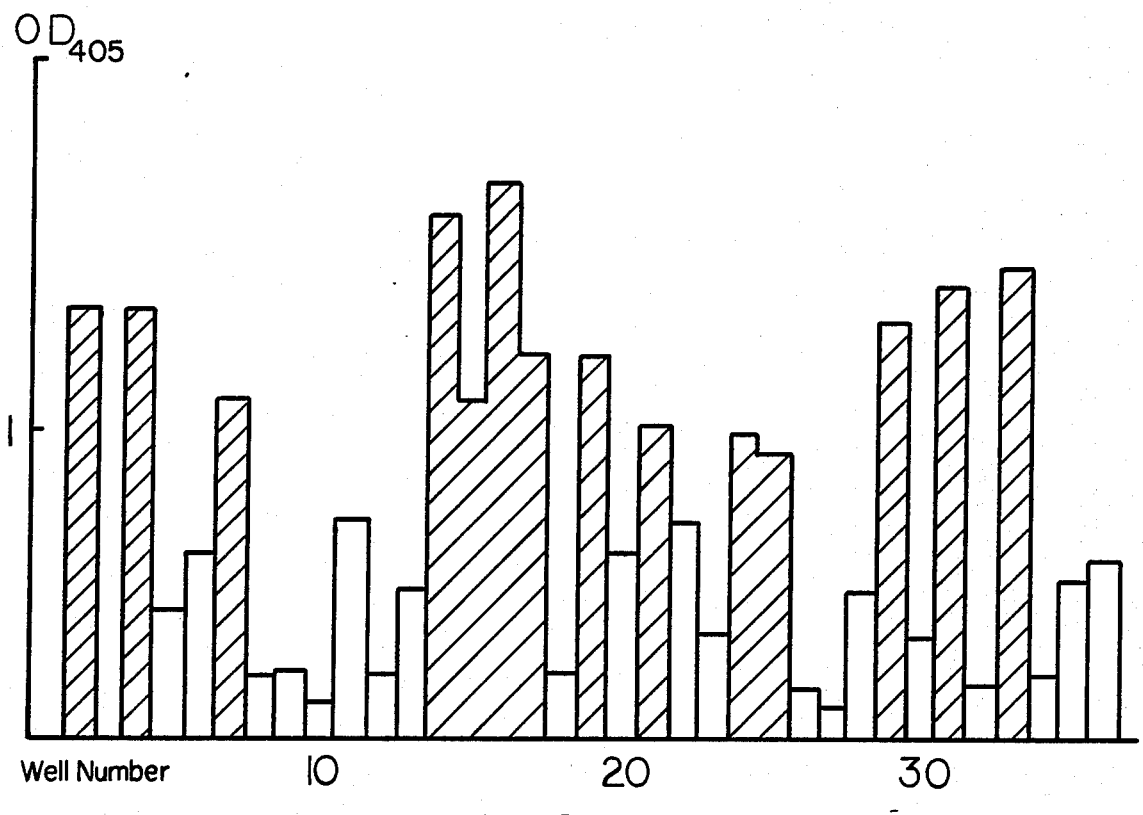
FIG. 1: Results of an enzyme-linked immunosorbent assay (ELISA) for anti-nortriptyline antibodies in the supernatants of cultures of TP-3 cells fused with splenocytes from rabbits immunized with nortriptyline (NT).

The methods of preparing the TP-3 cell line and the hybrid cells and of producing and characterizing the monoclonal antibody generally comprise the following steps:

A. Producing the TP-3 cell line by transforming rabbit splenocytes with SV40 and subsequently causing mutagenesis to occur by exposure of the cells to EMSF. After exposure to EMSF, the cells are selected for various characteristics. The resultant cell line is HGPRT$^-$, extremely sensitive to HAT, fast growing, has a very low level of revertants, and grows continuously.

B. Immunizing rabbits with immunogens. Any known immunogen can be used. The immunization schedule and immunogen concentration should be such as to produce useful quantities of suitably primed antibody-producing cells. These immunization protocols are generally well known or can be worked out using known principles, and will vary depending on the immunogen.

C. Removing the lymphoid tissue containing the antibody-producing cell from the immunized rabbits and making a single cell suspension. These techniques are well known.

D. Fusing the antibody-producing cells from the immunized rabbits with the TP-3 cells with the use of a suitable fusion promoter. The preferred cellular ratio for fusion is about 10 antibody-producing cells per TP-3 cell. The preferred fusion promoter is polyethylene glycol 1500 (PEG), but other fusion promoters known in the art may be used.

E. Diluting and culturing the fusion cell mixture in HAT-containing medium. The HAT-containing medium will not support the unfused TP-3 cells, and they will die. Since the unfused antibody-producing cells divide only a finite number of times, they fail to reproduce after a certain period of time. The fused cells continue to reproduce because they possess the immortal quality of the TP-3 parent cell and the ability of the antibody-producing parent cell to survive in the HAT-containing medium. The cell concentration is statistically calculated to isolate a certain number of cells in each separate container which makes it probable that the resultant clones derive from a single hybrid cell.

F. Evaluating the supernatant in each container by known screening tests. Supernatants from containers containing hybrid cells (as evidenced by detectable cell growth in the container) were tested to determine if IgG immunoglobulin was present and to determine if antibody to the immunogen was present. If antibody to the immunogen was detected, it was further characterized by known procedures. Although only testing procedures which detect the IgG class of immunoglobulin were employed, the procedures for detecting the other classes of immunoglobulins are well known, and it is not intended that the invention be limited to the IgG class of monoclonal antibody. Monoclonal antibody of the IgM, IgA, IgE or IgD classes may also be produced and are intended to be part of the invention.

G. Selecting and cloning hybrid cells by limiting dilution.

H. Putting the selected and cloned cells into continuous cell culture.

I. Producing monoclonal antibody. Once the desired hybrid cell has been selected and cloned, the resultant antibody may be produced by in vitro culturing of the desired hybrid cell in a suitable medium for a suitable length of time, followed by recovery of the desired antibody from the supernatant. The suitable medium and suitable length of culturing time are known or can be readily determined. Alternatively, it should be possible to inject hybrid cells into irradiated rabbits or into nude mice where they will cause the formation of the desired antibody in the bloodstream and peritoneal exudate of the host after a suitable incubation time.

EXAMPLE I

Production of the TP-3 Cell Line

The TP-3 cell line was derived from rabbit splenocytes. The rabbit splenocytes were transformed by SV40 using the method of J. J. Collins et al. *P.N.A.S.*, 71. 260–62 (1974), to produce the TRSC-1 cell line. Mutagenesis of the TRSC-1 cell line was accomplished by exposure of the cells to 0.02% EMSF. Exposure to EMSF was followed by selection in 6-thioguanine-containing medium to obtain a stable HGPRT$^-$ mutant cell line. The cells were further selected for their extreme sensitivity to HAT, for a very low level of revertants, and for fast growth capability in RPMI 1640 tissue culture medium (purchased from Boehringer Mannheim) containing 10% Fetal Calf Serum (FCS).

The TP-3 cells which were thus selected were placed in continuous culture. Cultures of the TP-3 cells were divided into subcultures when cell growth became too heavy by placing a known number of the cells in fresh RPMI 1640 containing 10% FCS. The TP-3 cells have remained stable after several years in continuous culture.

Tests indicate that the TP-3 cell line has maintained its rabbit nature throughout the years of continuous culture. Rabbit $\beta$-microglobulin is still detectable on the surface of the TP-3 cells, and electrophoresis on agarose gels of the DNA of TP-3 cells which has been digested with restriction enzymes give patterns identical to those of normal rabbit DNA similarly digested. Further, the use of a specific DNA probe which hybridizes only with the C kappa gene of rabbit DNA hybridizes with the TP-3 cell line DNA. Finally, cells of the TP-3 cell line are, of course, descendants of rabbit splenocytes.

Samples of the TP-3 cell line were deposited on Mar. 27, 1985, with the American Type Culture Collection (ATCC), Rockville, Md. The cell line was assigned deposit number CRL 8761.

Cells of the TP-3 cell line were fused, as will be described in greater detail below, with lymphocytes from rabbits immunized with various antigens to produce hybrid cells capable of producing monoclonal antibody.

EXAMPLE II

Methods of Immunizing Rabbits

1. Immunization With Nortriptyline: Nortriptyline (NT) was coupled to succinylated bovine serum albumin (SBSA) using 1-cyclohexyl-3-(2-morpholinoethyl)-carbodiimide-metho-p-toluene sulfonate (Aldrich C10,640-2). After coupling, the SBSA-NT was dissolved in 10 mM phosphate buffered saline (PBS), pH 7.4, at a concentration of 1.0 mg/ml. Then 1.0 ml of this solution was emulsified in an equal volume of Complete Freund's Adjuvant (CFA), and the emulsion was injected intradermally at multiple sites on each of several rabbits. Fifteen days later, 1.0 ml of SBSA-NT at 1.0 mg/ml was emulsified in an equal volume of Incomplete Freund's Adjuvant (IFA), and the emulsion was injected subcutaneously at one site on each rabbit. One week later, the polyclonal antibody response of the rabbit was evaluated by performing an ELISA test (see description of ELISA testing below). Six months later and three days before fusion with TP-3 cells, the rabbits were given an intravenous booster injection of 0.1 mg. of SBSA-NT in 0.5 ml PBS, pH 7.4.

2. Immunization With Human Hepatitis B Virus Surface Antigen (HBSAg): A solution of HBSAg in normal saline at 50 micrograms per ml was emulsified with an equal volume of CFA. Then 1.0 ml of the emulsion was injected intradermally at multiple sites on each of several rabbits. Fifteen days later, 1.0 ml of an emulsion of IFA and an equal volume of HBSAg in PBS, pH 7.4, at 1.0 mg/ml was injected subcutaneously at one site on each rabbit. An intravenous booster injection of 0.5 ml of a 0.1 mg/ml solution of antigen in saline was administered three days prior to fusion.

3. Immunization with Alprenolol:

Alprenolol (alp) was coupled to a protein such as BSA. The coupling was done as described by S. Chamat, J. Hoebeke and A. D. Strosberg in the *Journal of Immunology*, 133, 1547–52 (1984). The BSA-alprenolol (BSA-alp) complex was suspended in 10 mM PBS, pH 7.4, at a concentration of 1.0 mg/ml. Two ml of this suspension was mixed with an equal volume of CFA and was then injected intradermally at multiple sites on each of several rabbits. One month later, a subcutaneous injection of 1.0 ml of antigen at 1.0 mg/ml emulsified with an equal volume of IFA was given. A booster injection of 0.5 mg of BSA-alp in IFA was given three days prior to fusion. The presence of polyclonal antibodies to alp was tested for by an ELISA test (see detailed description of ELISA below).

EXAMPLE III

Fusion of TP-3 Cells With Immunized Rabbit Splenocytes Or Gangliocytes

A single cell suspension of the splenocytes of immunized rabbits was obtained by injection of tissue culture medium into the spleen to disrupt the capsule. The TP-3 cells and splenocytes were then mixed at a ratio of 10 splenocytes per TP-3 cell. Fusion was accomplished by slowly adding 2.0 ml of PEG (Merck Art. 807489) at a concentration of 41% in RPMI 1640 per $10^8$ splenocytes. The fusion mixture was then incubated for one minute at 37° C. and subsequently centrifuged at 2000 rpm 10 minutes 25°. The cells were washed once with RPMI 1640 and were finally resuspended in RPMI 1640 containing 10% FCS at a cellular concentration of $2 \times 10^6$ splenocytes/ml.

The fused cell suspension was then aliquoted into NUNC brand tissue culture plates. One ml was added to each well of two NUNC 24-well plates. The cells were incubated at 37° C. in an atmosphere containing 10% $CO_2$. The day on which culturing began was taken as Day 0. On Days 1, 4, 7 and 11, the cultures were fed by partially replacing the culture medium with HAT Medium (RPMI 1640 containing 10% FCS and HAT).

The HAT Medium selects for hybrid cells since the TP-3 cells are extremely HAT sensitive and will not grow in HAT-containing medium, and splenocytes will die after several days of culture. Further, culturing of the cells at low cellular concentrations such as those used makes it highly probable that clones of cells derived from a single hybrid cell will be produced. To insure that clones of a single hybrid cell are obtained, the hybrid cells were further selected by limiting dilution. Clones derived from a single hybrid cell produce monoclonal antibody.

The hybrid cell clones and subclones obtained have been placed in continuous culture. Cultures of the hybrid cells were subdivided into cell cultures when cell growth became too heavy by placing a known number of the cells in fresh RPMI containing 10% FCS.

Samples of a hybrid cell line producing monoclonal antibodies to alp were deposited with the ATCC on Apr. 4, 1985. This hybrid cell line was assigned deposit number HB 8776.

Initially the hybrid cells obtained were adherent cells. The adherent nature of the hybrid cells made it difficult to grow large batches of the cells. Hybrid cells that grow in suspension were selected by growing them on NUNC Fibroblast Primaria plates which are culture plates specially treated so that cells tend not to adhere to the plates. The medium used was RPMI 1640 containing 10% FCS.

Having a hybrid cell line growing in suspension made it possible to grow large batches of the cells and should make it possible to inject and grow the cells in irradiated rabbits or nude mice. Growing the hybrid cells in large quantities or in animals means that large amounts of monoclonal antibody can be obtained.

Ganglion cells from immunized rabbits were also fused with TP-3 cells using the same protocol as described above for rabbit splenocytes.

Fusion between immunized rabbit cells and LICR-LON-HMY-2 cells was also attempted using the same protocol as described above except that the ratio of splenocytes to LICR-LON-HMY-2 used was about 25:1. LICR-LON-HMY-2 is an 8-azaguanine-resistant human plasmacytoma cell line which has been described by K. M. Burk, et al. in *Cancer Res.*, 38, 2508–2513 (1978) and P. A. W. Edwards, et al. in *Nature*, 300, 264–67 (1982). The attempts to fuse rabbit splenocytes with LICR-LON-HMY-2 were unsuccessful, and no hybrid cells were produced. Accordingly, the supernatants of these cultures were used as negative controls in some of the screening tests.

EXAMPLE IV

Screening Tests

The supernatants from the fused cell cultures were tested by one of several screening tests to detect and characterize the antibodies. In addition, the ELISA tests described below were used to monitor the appearance of polyclonal antibodies in the immunized rabbits.

1. Nortriptyline Screening Tests a. ELISA for Nortriptyline (NT) Antibodies: On Day 15 of culture, an ELISA test was performed on the supernatants of the fused cell cultures to determine if antibodies to NT were present. The test was performed as follows. A lysozyme-nortriptyline conjugate (LNT) was prepared using the technique described by Kamel et al in Clin. Chem., 25, 1997 (1979). The LNT was used to coat the wells of polystyrene plates (NUNC microtiter plates, #96F2-39454). To coat the wells, 50 microliters of a 5 microgram per ml. solution of LNT in 10 mM PBS, pH 7.4, were added to each well. The plates were then incubated at room temperature for 90 minutes. Free absorption sites were saturated with 3% BSA in PBS. Then 0.05 ml of each of the culture supernatants was added to the wells, and the plates were incubated for 60 minutes at room temperature. Then 0.05 ml of goat anti-rabbit antibody coupled to peroxydase (GAR-peroxydase) at an appropriate dilution was added, and the plates were incubated for 90 minutes at room temperature. After washing, 0.2 ml of the substrate 2,2-azino-di-3-ethylbenzthiazoline sulfonic acid (ABTS) (Sigma Ref. A1888) was added. The presence of antibodies to NT was demonstrated by an increase in absorbance at 405 nm.

In FIG. 1, the results of the ELISA test for anti-NT antibodies in culture supernatants is presented. The optical density of the solution (OD) at a wavelength of 405 nm is shown on the ordinate and the number of the well being tested is shown on the abscissa. As can be seen from examining FIG. 1, 14 out of 35 wells were positive (cross-hatched bars indicate positive wells) showing that hybrid cells producing antibodies to NT were present in 14 of 35 wells. The thirty-five wells which were tested were chosen because of the presence of cellular growth in those wells. The positive clones have been given designations HYL-1 to HYL-14.

b. Sandwich ELISA Test For IgG: The wells of polystyrene NUNC microtiter plates were coated with 0.05 ml of goat anti-rabbit IgG antibody at an appropriate concentration. After washing, 0.05 ml of the supernatants from the cultures of TP-3 cells fused with splenocytes from rabbits immunized with NT were added to the coated wells. The plate was then incubated for 60 minutes at room temperature. Finally, 0.05 ml of GAR-peroxydase was added to each well. After incubating for 60 minutes at room temperature, 0.2 ml of ABTS at 0.2 mg/ml in 10 mM PBS, pH 7.4, was added. The increase in absorbance at 405 nm was monitored.

Figure 2:
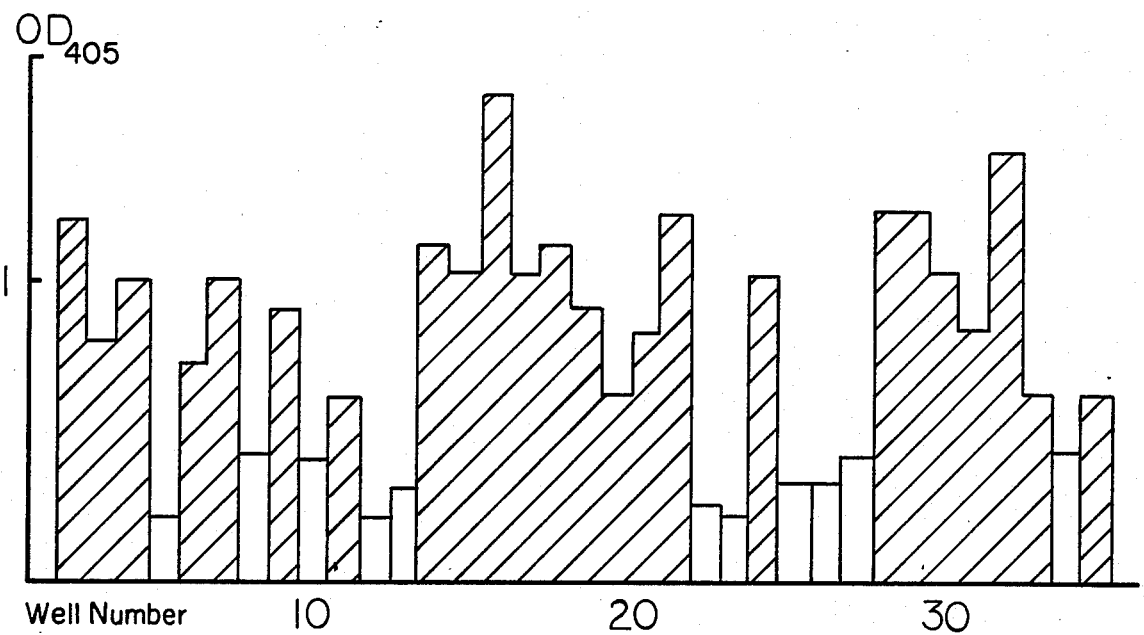
FIG. 2: Results of a sandwich enzyme-linked immunosorbent assay (Sandwich ELISA) for rabbit IgG antibodies in the supernatants of cultures of TP-3 cells fused with splenocytes from rabbits immunized with NT.

The results of the Sandwich ELISA test of the supernatants from the same 35 wells as were tested in the ELISA are shown in FIG. 2. It was found that 24 out of 35 wells were positive (cross-hatched bars) indicating that IgG antibodies were being produced by the hybrid cells in 24 out of 35 wells.

Wells positive in the ELISA test for NT but negative in this Sandwich ELISA test may contain hybrid cells which secrete antibodies to NT of the IgM or IgA class not identified by the goat anti-rabbit IgG antibodies used in the Sandwich ELISA test. Wells positive in this Sandwich ELISA test but negative in the ELISA test contain secreted IgG which has no activity towards NT. Wells positive in both the ELISA test and the Sandwich ELISA test contain hybrid cells producing IgG antibodies to NT.

c. Secretion Test: The fourteen positive hybrid clones which were identified in the above ELISA test were subcloned by limiting dilution. The subclones were given designations HYL-1$^S$ through HYL-14$^S$ with subclone HYL-1$^S$ being derived from clone HYL-1, HYL-2$^S$ being derived from clone HYL-2, etc. The supernatants of the subclones were tested for binding to LNT by the above-described ELISA test at different growing stages. As is shown in FIG. 3, day 4 was the first day on which the ELISA test was positive, and eight subclones were positive (cross-hatched bars) on Day 7 of culture as shown by this ELISA test. In fact, the signal actual increased during the seven days of culture.

Figures 4A, 4B:
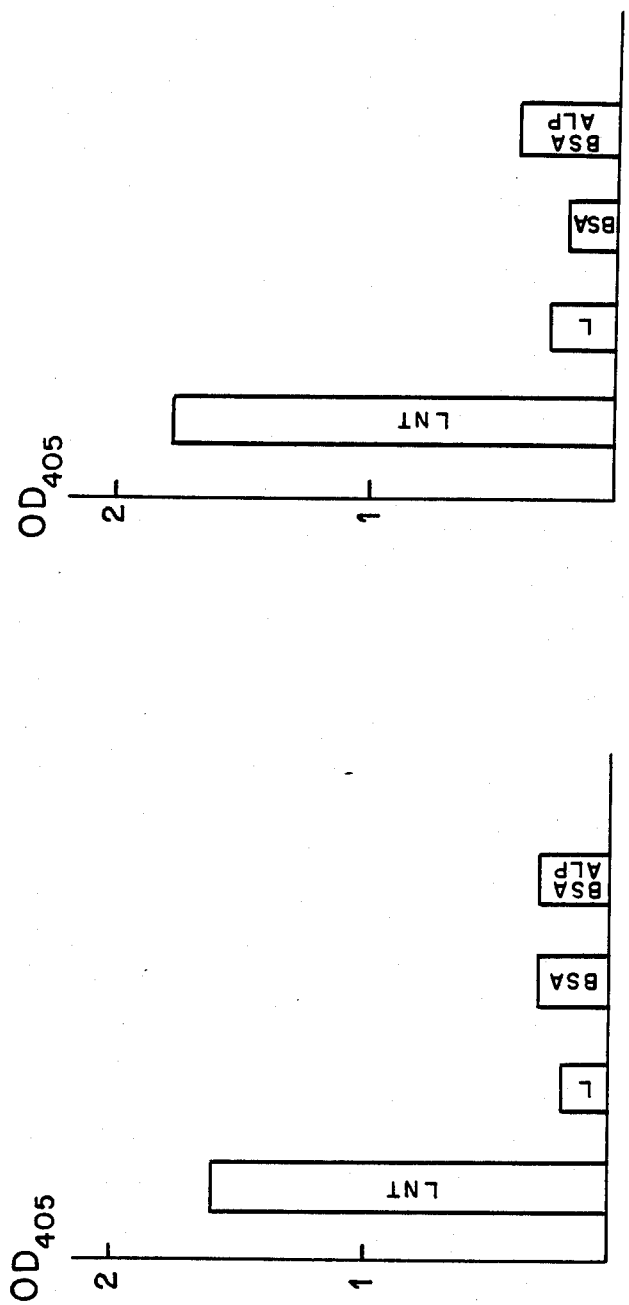
FIG. 4: Results of ELISA tests for specificity of the supernatants from cultures of two of the most positive hybrid cell clones from the fusion of TP-3 cells with splenocytes from rabbits immunized with NT using two different hapten-carrier conjugates.

Subcloning by limiting dilution makes it virtually certain that the antibodies that were detected were monoclonal antibodies being produced by cells derived from a single hybrid cell. Further, the fact that Day 4 was the first day on which the ELISA test was positive and the fact that the positive response actually increased through Day 7 shows that the detected antibodies were actually being made and secreted by the hybrid cells.

d. Control Of Specificity: The supernatants of cultures of two of the most positive and stable hybrid cell subclones, those designated as HYL-1$^S$ and HYL-14$^S$, were tested by ELISA tests using two hapten-carrier conjugates BSA-alp and LNT. The results in FIG. 4 show that these two hybrid cell clones produce antibody having a narrow specificity for NT (part A of FIG. 4 shows the results for HYL-1$^s$ and part B shows the results for HYL-14$^s$). The fact that the antibody is specific for NT is further evidence that the antibody is monoclonal antibody.

e. DEAE Cellulose Chromatography: Positive supernatants from cultures of hybrid cell clones and subclones thereof were pooled and then chromatographed on a DEAE-cellulose column in 0.0175 M PBS at pH 6.3. The various immunoglobulin fractions were eluted, and the eluted fractions were tested using the ELISA test for NT described above. The peak eluting with IgG contained anti-NT activity, and none of the other peaks contained anti-NT activity. The fact that all of the antibody to NT secreted by the hybrid cells was of a single immunoglobulin class is further evidence of the monoclonality of the antibody.

f. Intrinsic Labeling By $^{35}$S Methionine: Hybrid cells of the clones designated HYL 1 and HYL 14 were cultured for twelve hours in the presence of 10 uCi of $^{35}$S-methionine. The supernatants were harvested, lyophilized and then solubilized in sodium dodecyl sulfate (SDS). The SDS-solubilized material was electrophoresed on polyacrylamide gels or on cellulose acetate plates. A single radioactive band in the immunoglobulin region was detected upon electrophoresis. The fact that the antibody possesses a single electrophoretic mobility indicates that the antibody is monoclonal antibody.

g. Test for Allotypic Markers: The IgG antibodies of rabbits have antigenic determinants called allotypic markers. The presence of rabbit allotypic markers (series a and b) on the immunoglobulins secreted by the hybrid cells into the supernatants from positive cultures was demonstrated by a microELISA test using rabbit anti-allotype (Fab)'2 fragments.

Specific anti-allotypic sera were prepared, and the various immunoglobulin fractions were obtained by DEAE cellulose chromatography. Then, digestion with pepsin was performed on each immunoglobulin fraction to obtain the (Fab')$_2$ fractions. The (Fab')$_2$ fractions were coated (10ug/ml) on NUNC microtiter plates. The presence of the various allotypic markers on the IgG in the supernatants was revealed by adding specific goat anti-rabbit Fc labelled with peroxydase. After washing, ABTS was added and the absorbance at 405 nm was monitored.

The allotypes of the IgG of the parent cells were al al b4 b4 and al a3 b4 b4. The IgG allotype secreted by the hybrid cells was show to be al al b4 b4. The fact that only one allotype was secreted is further evidence that the secreted antibody is monoclonal antibody.

2. Screening Tests For HBSAg a. Radioimmunoassay (RIA) Test for Human Hepatitis B Virus Surface Antigen (HBSAg): A RIA test for HBSAg was performed. Beads were labeled with HBSAg according to the protocol used in the Abbott Laboratories HBSAg screening test. The culture supernatants presumed to contain the antibody were added to the coated beads, and the mixture was incubated overnight at 25° C. After washing the beads, 0.2 ml of $^{125}I$-labeled HBSAg was added, and antibody binding was revealed after incubation for 4 hours at 25° C. by counting the washed beads in a gamma counter.

Figure 5:
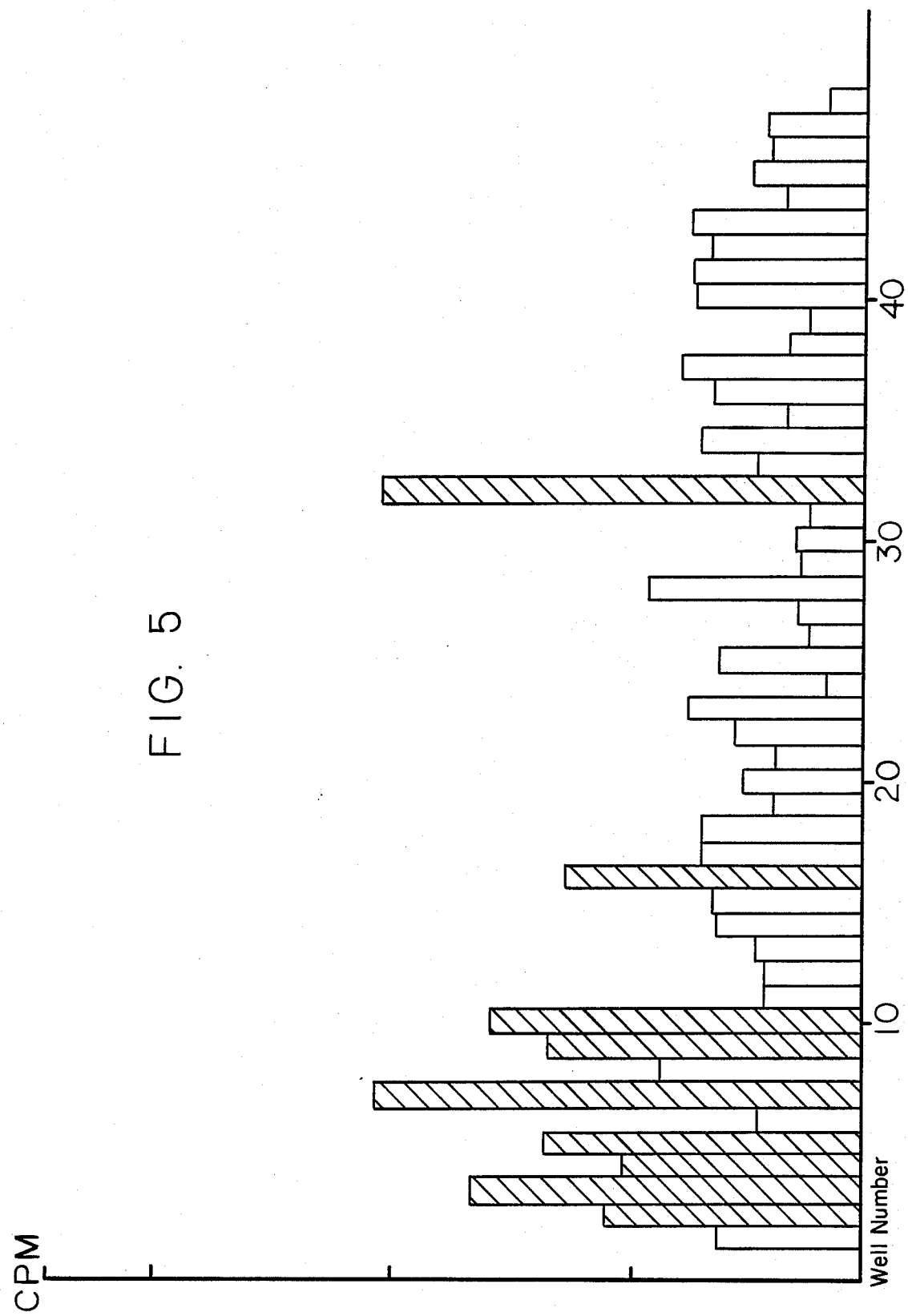
FIG. 5: Results of a radioimmunoassay (RIA) test for anti-human hepatitis B virus surface antigen (HBSAg) antibodies in the supernatants of cultures of TP-3 cells fused with splenocytes from immunized rabbits.

The results of the RIA test of the supernatants of cultures of TP-3 cells fused with splenocytes from rabbits immunized with HBSAg are shown in FIG. 5 and show that 9 out of 48 cultures contained hybrid cells producing antibody to HBSAg (cross-hatched bars). The 48 supernatants tested were chosen because cell growth was observed in these wells.

b. Sandwich ELISA Test: Goat anti-rabbit IgG at an appropriate dilution in 10 mM PBS, pH 7.4, was added to the wells of NUNC polystyrene plates, and the plates were incubated for 60 minutes at 37° C. Free absorption sites were saturated with 0.1 ml of gelatin Tween at 2.5 mg/ml in 10 mM PBS, pH 7.4, and 0.05 ml of cell culture supernatants were then added to the wells. The plates were incubated for 60 min. at 37° C. Antibody binding was revealed by the addition of 0.05 ml GAR peroxydase at an appropriate dilution followed by the addition of 0.2 ml of 0.02 mg/ml ABTS substrate. The cleavage of ABTS was monitored at 405 nm.

Figure 6:
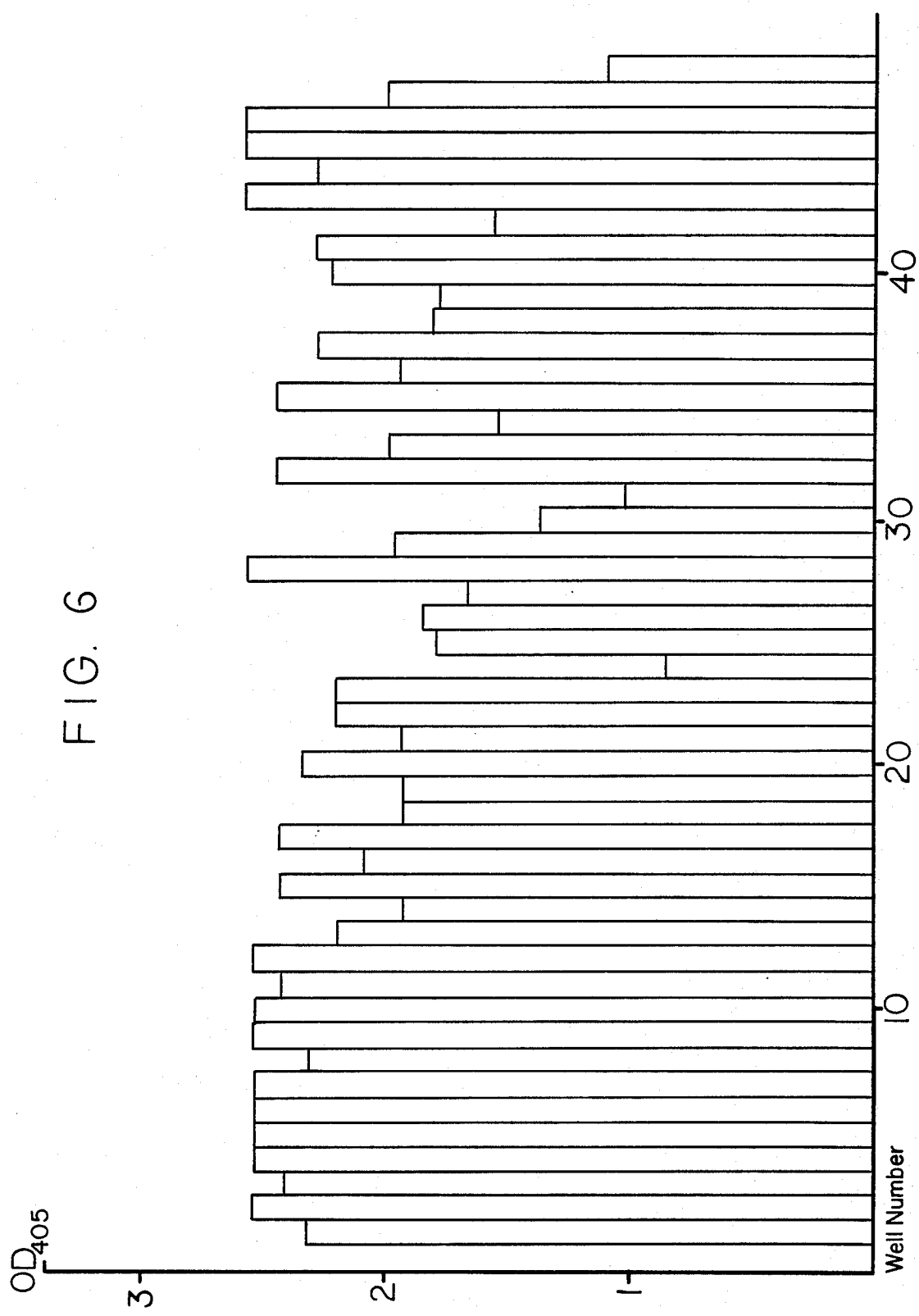
FIG. 6: Results of a sandwich ELISA test for rabbit IgG antibodies in the supernatants of cultures of TP-3 cells fused with splenocytes from rabbits immunized with HBSAg.

The results are shown in FIG. 6. As shown there, the supernatants from all 48 wells were positive, indicating the presence of IgG in all 48 wells. The combined results of the RIA and sandwich ELISA tests indicate that the hybrid cells are producing IgG antibodies to HBSAg.

3. Alprenolol Screening Test a. ELISA Test For Alprenolol: Keyhole limpet hemocyanin-alprenolol (KLH-alp) conjugate, 0.05 ml at a concentration of 0.015 mg/ml in 10 mM PBS, pH 7.4, was added to the wells of a NUNC polystyrene microtiter plate. The plates were incubated for one hour at room temperature. Non-specific sites of fixation were saturated by the addition 0.05 ml of gelatin-Tween, 0.2% in 10 mM PBS, pH 7.4, and the plates were incubated again for one hour at room temperature. Next, 50 μl of each of the culture supernatant and the plates were again incubated for one hour at room temperature. The plates were washed several times with PBS-gelatin-Tween. Next 0.05 ml GAR-peroxydase at an appropriate dilution in PBS-gelatin-Tween was added and the plates were incubated for one hour at room temperature. The plates are washed several times with PBS. Then, 0.2 ml of the substrate ABTS at 0.02 mg/ml in 10 mM PBS, pH 7.4, was added. The change in absorbance at 405 nm was measured.

Figure 7:
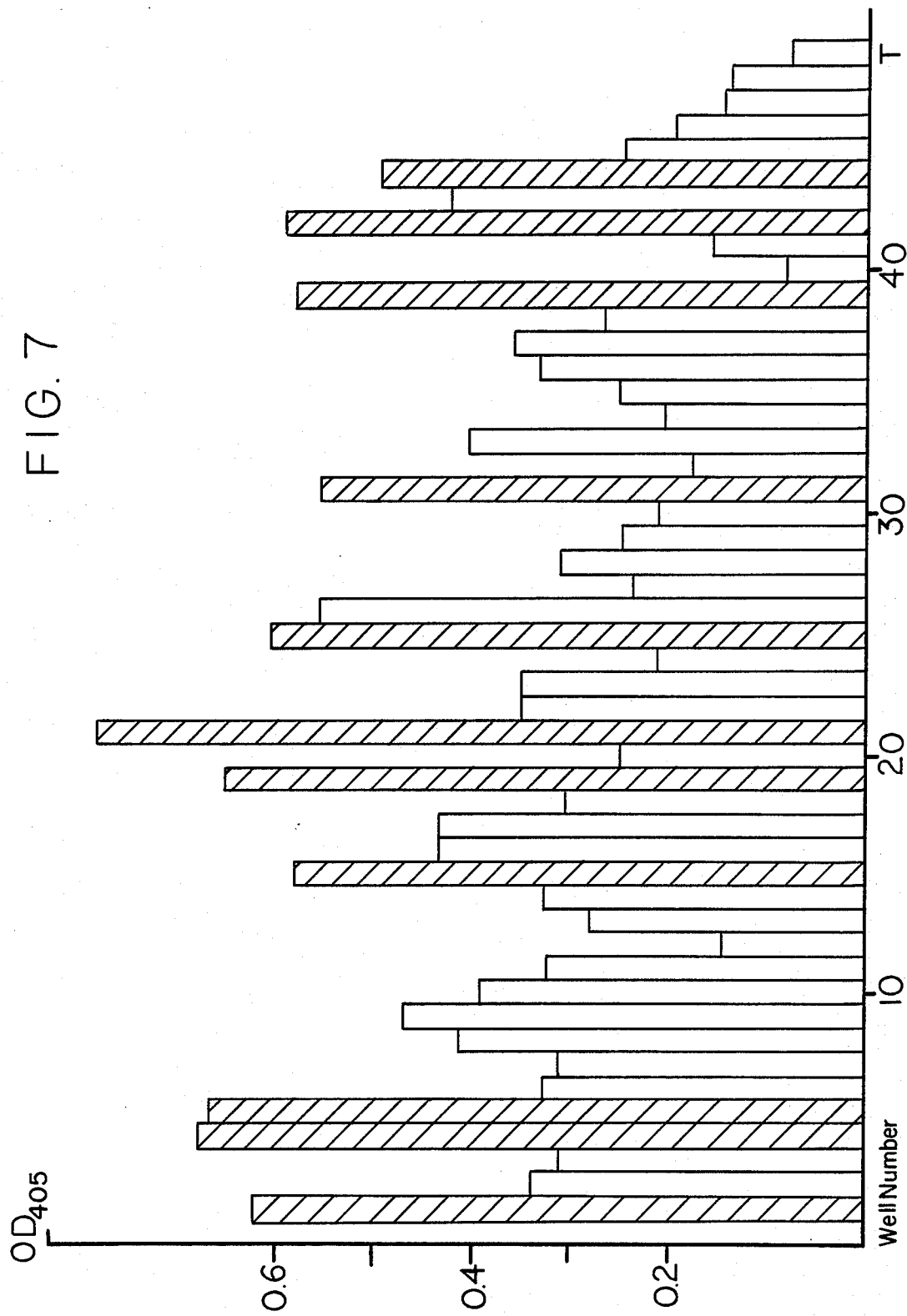
FIG. 7: Results of an ELISA test for antibodies to alprenolol (alp) in TP-3 cells fused with immunized splenocytes.

As shown in FIG. 7, the supernatants of cultures of TP-3 cells fused with splenocytes from alp-immunized rabbits contained antibody to alp in 11 out of 48 wells (cross-hatched bars), showing that hybrid cells making antibody to alp were present in those wells. In FIG. 7, the bar marked "T" is the negative control.

One of the positive cultures was given the designation HYL-L. It was cloned and put into continuous culture. It was this cell line which was deposited with the ATCC and which received deposit number HB 8776.

b. Intrinsic Labelling by $^{35}S$-Methionine: Positive clones were cultured for twelve hours in the presence of 10 uCi of $^{35}S$-methionine. TP-3 cells alone were also cultured with $^{35}S$-methionine under identical conditions. The supernatants were harvested, lyophilized and then SDS-solubilized. The SDS-solubilized material was electrophoresed for 40 minutes at 240 V on cellulose acetate plates. A single radioactive band in the immunoglobulin region was found upon electrophoresis of the supernatants produced during the culture of the positive clones, whereas no such band was detected upon electrophoresis of the supernatants produced during the culture of the TP-3 cells. The fact that a radioactive band was found in the immunoglobulin region means that $^{35}S$-methionine was incorporated into immunoglobulin synthesized by the cell during the culture period. This in turn shows that the positive clones are synthesizing and secreting antibody.

We claim:

1. A continuous rabbit cell line, designated TP-3 and deposited with the ATCC as culture CRL 8761, wherein said cells are:
   hypoxyxanthine-guanine-phosphoribosyl transferase deficient;
   hypoxyxanthine-aminopterine-thymidine sensitive;
   fast growing;
   non-antibody-secreting; and
   capable of fusing with antibody-producing rabbit cells to produce hybrid cells capable of continuous growth and of secreting antibody;
   and clones and subclones thereof.

2. A method of producing rabbit-rabbit hybrid cells comprising:
   fusing an antibody-producing rabbit cell with the rabbit cell line of claim 1; and
   selecting for the fused cells that can grow continuously and are capable of secreting antibody.

3. The method of claim 2 wherein the antibodyproducing rabbit cell is a splenocyte.

4. The rabbit-rabbit hybrid cell produced by the method of claim 3.

5. The rabbit-rabbit hybrid cell produced by the method of claim 2.

6. A method for producing rabbit monoclonal antibody comprising:
   immunizing a rabbit with an immunogen;
   fusing the antibody-producing cells from said rabbit with the cell line of claim I to produce a hybrid cell;
   selecting for said hybrid cell;
   culturing said selected hybrid cells; and
   collecting the antibody secreted by said cultured, hybrid cells.

7. The method of claim 6 wherein the antibody-produced cells are rabbit splenocytes.

8. The method of claim 7 wherein the immunogen is nortriptyline.

9. The method of claim 7 wherein the immunogen is human hepatitis B surface antigen.

10. The method of claim 7 wherein the immunogen is alprenolol.

11. A method of producing the cell line of claim 1 comprising:

transforming rabbit splenocytes with Simian-Virus 40;

treating the transformed cells with ethyl methyl sulfonate; and selecting for treated cells that can grow continuously and are: hypoxyxanthine-guanine-phosphoribosyl transferase deficient; hypoxyxanthine-aminopterine-thimidine sensitive; fast growing; non-antibody secreting and capable of using with antibody-producing rabbit cells to produce hybrid cells capable of continuous growth and of secreting antibody.

* * * * *

UNITED STATES PATENT AND TRADEMARK OFFICE
CERTIFICATE OF CORRECTION

PATENT NO. : 4,859,595
DATED : August 22, 1989
INVENTOR(S) : Arthur D. Strosberg et al.

It is certified that error appears in the above-identified patent and that said Letters Patent is hereby corrected as shown below:

In column 2, line 37, please delete "ESF" and substitute therefor --EMSF--.

In column 5, line 65, after "rpm" please insert --for--; after "minutes" insert --at--; and delete "25°" and substitute therefor --25°C--.

In column 6, line 5, please delete "CO2" and substitute therefor --$CO_2$--.

In column 8, line 25, after "conjugates" please insert --:--.

In column 9, line 34, please delete "gelatin Tween" and substitute therefor --gelatin-Tween--.

In column 9, lines 38 and 39, please delete "GAR peroxydase" and substitute therefor --GAR-peroxydase--.

In column 9, line 45, please delete "sandwich" and substitute therefor --Sandwich--.

In column 9, line 59, please delete "supernatant" and substitute therefor --supernatants was added,--.

UNITED STATES PATENT AND TRADEMARK OFFICE
CERTIFICATE OF CORRECTION

PATENT NO. : 4,859,595

DATED : August 22, 1989

INVENTOR(S) : Arthur D. Strosberg et al.

It is certified that error appears in the above-identified patent and that said Letters Patent is hereby corrected as shown below:

In claim 3, column 10, lines 49 and 50, please delete "antibodyproducing" and substitute therefor --antibody-producing--.

In claim 6, column 10, line 63, after "cultured" please delete --,--.

In claim 7, column 10, lines 66 and 67, please delete "antibody-produced" and substitute therefor --antibody-producing--.

In claim 11, column 12, line 7, please delete "using" and substitute therefor --fusing--.

Signed and Sealed this

Twenty-third Day of June, 1992

Attest:

DOUGLAS B. COMER

*Attesting Officer*     *Acting Commissioner of Patents and Trademarks*